US008318236B2

(12) United States Patent
Van Sciver et al.

(10) Patent No.: US 8,318,236 B2

(45) Date of Patent: *Nov. 27, 2012

(54) STENT COATING METHOD

(75) Inventors: Jason Van Sciver, Los Gatos, CA (US); Yung-Ming Chen, Cupertino, CA (US); Lothar Kleiner, Los Altos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/162,937

(22) Filed: Jun. 17, 2011

(65) Prior Publication Data

US 2011/0244112 A1 Oct. 6, 2011

Related U.S. Application Data

(63) Continuation of application No. 11/305,662, filed on Dec. 16, 2005, now Pat. No. 7,976,891.

(51) Int. Cl.

*B05D 1/02* (2006.01)
*A61F 2/06* (2006.01)
*B41J 2/04* (2006.01)
*B41J 2/06* (2006.01)

(52) U.S. Cl. ....... 427/2.24; 427/2.1; 427/2.25; 427/425; 427/427.2; 347/54; 347/55; 347/75

(58) Field of Classification Search .................. 427/2.1, 427/2.24, 2.25, 261, 457, 565; 347/46, 48, 347/75

See application file for complete search history.

(56) References Cited

U.S. PATENT DOCUMENTS

| | | | | |
|---|---|---|---|---|
| 4,697,195 | A | 9/1987 | Quate et al. | |
| 4,733,665 | A | 3/1988 | Palmaz | |
| 4,800,882 | A | 1/1989 | Gianturco | |
| 4,886,062 | A | 12/1989 | Wiktor | |
| 5,722,479 | A | 3/1998 | Oeftering | |
| 5,898,446 | A | 4/1999 | Moriyama | |
| 6,217,151 | B1 | 4/2001 | Young | |
| 6,395,326 | B1 * | 5/2002 | Castro et al. | 427/2.24 |
| 6,596,239 | B2 | 7/2003 | Williams et al. | |
| 6,642,061 | B2 * | 11/2003 | Ellson et al. | 436/180 |
| 6,645,547 | B1 | 11/2003 | Shekalim et al. | |
| 6,676,987 | B2 * | 1/2004 | Zhong et al. | 427/2.24 |
| 6,867,248 | B1 | 3/2005 | Martin et al. | |
| 6,916,379 | B2 | 7/2005 | Shekalim et al. | |

(Continued)

FOREIGN PATENT DOCUMENTS

EP 0 586 187 3/1994

(Continued)

OTHER PUBLICATIONS

International Search Report for PCT/US2007/009113 filed Apr. 13, 2007, mailed Sep. 28, 2007, 15 pgs.

(Continued)

*Primary Examiner* — Timothy Meeks
*Assistant Examiner* — Cachet Sellman
(74) *Attorney, Agent, or Firm* — Squire Sanders (US) LLP

(57) ABSTRACT

A stent is coated by ejecting droplets of a coating substance from a reservoir containing a coating substance. A reservoir housing can have a plurality of reservoir compartments. A transducer is used to eject the coating substance from the reservoir. Energy from the transducer is focused at a meniscus or an interface between the coating substance and another coating substance in the reservoir.

14 Claims, 4 Drawing Sheets

U.S. PATENT DOCUMENTS

| | | | |
|---|---|---|---|
| 6,971,813 | B2 | 12/2005 | Shekalim et al. |
| 7,048,962 | B2 | 5/2006 | Shekalim et al. |
| 7,208,190 | B2 | 4/2007 | Verlee |
| 7,214,759 | B2 | 5/2007 | Pacetti et al. |
| 7,323,210 | B2 | 1/2008 | Castro et al. |
| 7,342,670 | B2 | 3/2008 | Teichman |
| 7,344,599 | B2 | 3/2008 | Shekalim et al. |
| 7,416,609 | B1 | 8/2008 | Madriaga et al. |
| 7,455,876 | B2 | 11/2008 | Castro et al. |
| 7,599,727 | B2 | 10/2009 | Teichman |
| 7,976,891 | B1 | 7/2011 | Van Sciver et al. |
| 2004/0053381 | A1 | 3/2004 | Williams et al. |
| 2004/0068316 | A1 | 4/2004 | Schaeffer |
| 2004/0076747 | A1 | 4/2004 | Shekalim et al. |
| 2004/0117007 | A1 | 6/2004 | Whitbourne et al. |
| 2004/0185081 | A1 | 9/2004 | Verlee et al. |
| 2004/0202773 | A1 | 10/2004 | Verlee et al. |
| 2004/0254634 | A1 | 12/2004 | Verlee et al. |
| 2005/0048194 | A1 | 3/2005 | Shmulewitz |
| 2005/0058768 | A1 | 3/2005 | Teichman |
| 2005/0212869 | A1 * | 9/2005 | Ellson et al. .................... 347/75 |
| 2005/0241577 | A1 | 11/2005 | Shekalim et al. |
| 2006/0073265 | A1 | 4/2006 | Teichman et al. |
| 2006/0136048 | A1 | 6/2006 | Pacetti et al. |
| 2006/0156976 | A1 | 7/2006 | Shekalim et al. |
| 2006/0172060 | A1 | 8/2006 | Teichman et al. |
| 2006/0217801 | A1 | 9/2006 | Rosenthal |
| 2006/0233942 | A1 | 10/2006 | Shekalim |
| 2008/0003349 | A1 | 1/2008 | Van Sciver et al. |
| 2008/0206442 | A1 | 8/2008 | Shekalim et al. |
| 2008/0220174 | A1 | 9/2008 | Teichman |
| 2008/0226812 | A1 | 9/2008 | Chen |
| 2009/0232964 | A1 | 9/2009 | Chen |

FOREIGN PATENT DOCUMENTS

| | | |
|---|---|---|
| EP | 0 728 584 | 8/1996 |
| EP | 1 364 628 | 11/2003 |
| WO | WO 2004/012784 | 2/2004 |

OTHER PUBLICATIONS

International Search Report for PCT/US2006/015541, filed Apr. 18, 2006, mailed Jun. 29, 2007, 18 pgs.

Elrod et al., "Nozzleless droplet formation with focused acoustic beams", J. of Applied Physics 65, No. 9, pp. 3441-3447 (1989).

Pouton et al., "Biosynthetic polyhydroxyalkanoates and their potential in drug delivery", Advanced Drug Delivery Reviews 18, pp. 133-162 (1996).

* cited by examiner

STENT COATING METHOD

CROSS-REFERENCE TO RELATED APPLICATION

This application is a continuation of application Ser. No. 11/305,662, filed Dec. 16, 2005, now U.S. Pat. No. 7,976,891, which is incorporated herein by reference.

TECHNICAL FIELD

This invention relates generally to stent coating apparatuses, and more particularly, but not exclusively, provides an assembly and method for coating of an abluminal stent surface by dispensing coating using acoustic energy.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Giantureo, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and the connecting elements 14 define a tubular stent body having an outer, tissue-contacting surface and an inner surface.

Stents are being modified to provide drug delivery capabilities. A polymeric carrier, impregnated with a drug or therapeutic substance is coated on a stent. The conventional method of coating is by, for example, applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer. The dipping or spraying of the composition onto the stent can result in a complete coverage of all stent surfaces, i.e., both luminal (inner) and abluminal (outer) surfaces, with a coating. However, having a coating on the luminal surface of the stent can have a detrimental impact on the stent's deliverability as well as the coating's mechanical integrity. Moreover, from a therapeutic standpoint, the therapeutic agents on an inner surface of the stent get washed away by the blood flow and typically can provide for an insignificant therapeutic effect. In contrast, the agents on the outer surfaces of the stent are in contact with the lumen, and provide for the delivery of the agent directly to the tissues. Polymers of a stent coating also elicit a response from the body. Reducing the amount to foreign material can only be beneficial.

Briefly, an inflatable balloon of a catheter assembly is inserted into a hollow bore of a coated stent. The stent is securely mounted on the balloon by a crimping process. The balloon is inflated to implant the stent, deflated, and then withdrawn out from the bore of the stent. A polymeric coating on the inner surface of the stent can increase the coefficient of friction between the stent and the balloon of a catheter assembly on which the stent is crimped for delivery. Additionally, some polymers have a "sticky" or "tacky" consistency. If the polymeric material either increases the coefficient of friction or adherers to the catheter balloon, the effective release of the stent from the balloon after deflation can be compromised. If the stent coating adheres to the balloon, the coating, or parts thereof, can be pulled off the stent during the process of deflation and withdrawal of the balloon following the placement of the stent. Adhesive, polymeric stent coatings can also experience extensive balloon sheer damage post-deployment, which could result in a thrombogenic stent surface and possible embolic debris. The stent coating can stretch when the balloon is expanded and may delaminate as a result of such shear stress.

Another shortcoming of the spray coating and immersion methods is that these methods tend to form defects on stents, such as webbing between adjacent stent struts 12 and connecting elements 14 and the pooling or clumping of coating on the struts 12 and/or connecting elements 14. In addition, spray coating can cause coating defects at the interface between a stent mandrel and the stent 10 as spray coating will coat both the stent 10 and the stent mandrel at this interface, possibly forming a clump. During removal of the stent 10 from the stent mandrel, this clump may detach from the stent 10, thereby leaving an uncoated surface on the stent 10. Alternatively, the clump may remain on the stent 10, thereby yielding a stent 10 with excessive coating.

Another shortcoming of the spray coating method is that a nozzle in a spray coating apparatus can get clogged with particulate when some of the coating substance solidifies. This clogging can deflect or block the spray, thereby yielding an unsatisfactory coating on the stent 10. The need to unclog a nozzle can cause long periods of downtime for a spray coating apparatus, thereby lowering production rates of stents.

Accordingly, a new apparatus and method are needed to enable selective coating of stent surfaces while minimizing the formation of defects and coating apparatus downtime.

SUMMARY OF THE INVENTION

Briefly and in general terms, the present invention is directed to a method of coating a stent.

In aspects of the present invention, a method comprises ejecting droplets of a coating substance with a transducer from a reservoir onto a stent strut, wherein the transducer is external to a reservoir housing having a plurality of reservoir compartments.

In aspects of the present invention, a method comprises ejecting droplets of a coating substance with a transducer from a reservoir onto a stent strut, wherein energy from the transducer is focused on a fluid meniscus of the coating substance, and causing the transducer to move with the fluid meniscus to maintain focus on the fluid meniscus as the fluid meniscus changes.

In aspects of the present invention, a method comprises ejecting droplets of a coating substance with a transducer from a reservoir onto a stent strut, wherein energy from the transducer is focused at an interface of the coating substance and a second coating substance in the reservoir.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF PREFERRED EMBODIMENTS

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
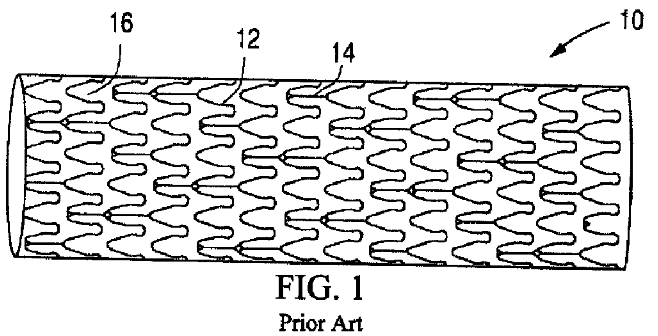
FIG. 1 Prior Art
FIG. 1 is a diagram illustrating a conventional stent.
Figure 2:
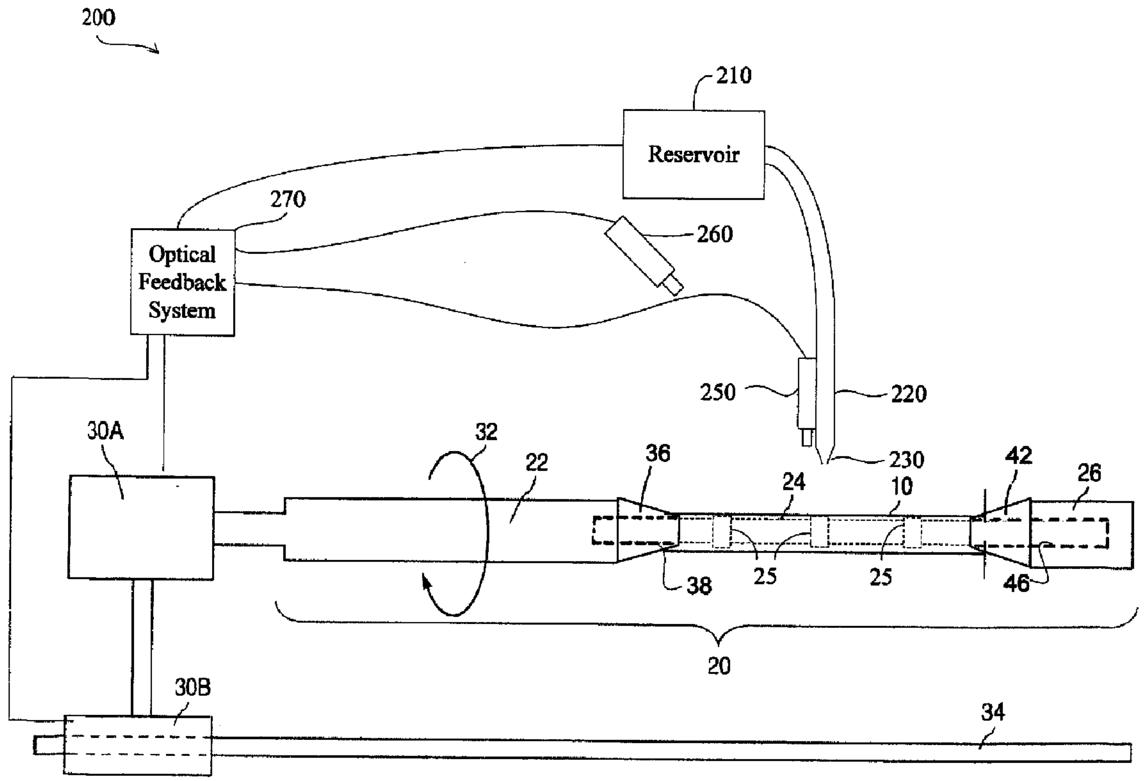
FIG. 2 is a block diagram illustrating a stent coating apparatus according to an embodiment of the invention.

FIG. 2 is a block diagram illustrating a stent coating apparatus 200 according to an embodiment of the invention. The apparatus 200, including a stent mandrel fixture 20 for supporting the stent 10, is illustrated to include a support member 22, a mandrel 24, and an optional lock member 26 (e.g., if the stent 10 can be supported by the mandrel 24 itself). The support member 22 can connect to a motor 30A so as to provide rotational motion about the longitudinal axis of the stent 10, as depicted by arrow 32, during a coating process. Another motor 30B can also be provided for moving the support member 22 in a linear direction, back and forth, along a rail 34.

The support member 22 includes a coning end portion 36, tapering inwardly. In accordance with one embodiment of the invention, the mandrel 24 can be permanently affixed to coning end portion 36. Alternatively, the support member 22 can include a bore 38 for receiving a first end of the mandrel 24. The first end of mandrel 24 can be threaded to screw into the bore 38 or, alternatively, can be retained within the bore 38 by a friction fit. The bore 38 should be deep enough so as to allow the mandrel 24 to securely mate with the support member 22. The depth of the bore 38 can also be over-extended so as to allow a significant length of the mandrel 24 to penetrate or screw into the bore 38. The bore 38 can also extend completely through the support member 22. This would allow the length of the mandrel 24 to be adjusted to accommodate stents of various sizes. The mandrel 24 also includes a plurality of ridges 25 that add rigidity and support to the stent 10 during the coating process. The ridges 25 have a diameter of slightly less than the inner diameter of stent 10. While three ridges 25 are shown, it will be appreciated by one of ordinary skill in the art that additional or fewer ridges may be present and they may be evenly or unevenly spaced.

The lock member 26 includes a coning end portion 42 tapering inwardly. A second end of the mandrel 24 can be permanently affixed to the lock member 26 if the first end is disengagable from the support member 22. Alternatively, in accordance with another embodiment, the mandrel 24 can have a threaded second end for screwing into a bore 46 of the lock member 26. The bore 46 can be of any suitable depth that would allow the lock member 26 to be incrementally moved closer to the support member 22. The bore 46 can also extend completely through the lock member 26. Accordingly, the stents 10 of any length can be securely pinched between the support and the lock members 22 and 26. In accordance with yet another embodiment, a non-threaded second end and the bore 46 combination is employed such that the second end can be press-fitted or friction-fitted within the bore 46 to prevent movement of the stent 10 on the stent mandrel fixture 20.

Positioned a distance from the stent 10 (e.g., above the stent 10) is a reservoir 210 holding a coating substance to be applied to the stent 10. The reservoir 210 is in fluid communication with an ejector 220 having an aperture 230. The ejector 220 is also positioned a distance from the stent 10 (e.g., above, below and/or at an angle to the stent 10). Disposed within the ejector 220 is a transducer 410 (FIG. 4) that converts electrical energy into vibrational energy in the form of sound or ultrasound. The sound or ultrasound (collectively referred to as acoustic energy herein) ejects (or dispenses) drops of the coating substance from the aperture 230 onto the stent 10. In an embodiment of the invention, each acoustic pulse from the transducer 410 dispenses a single drop from the aperture 230.

The reservoir 210 dispenses the coating substance to the ejector 220, which ejects it through the aperture 230, which will be discussed in further detail in conjunction with FIG. 4 below. The reservoir 210 can dispense the coating substance using gravity and/or forced pressure (e.g., a pump) to the ejector 220. The aperture 230 has a small opening of 50 μm to 250 μm and therefore the coating substance will not exit the aperture 230 due to surface tension and/or gravity unless the transducer 410 is activated. In an embodiment of the invention, if the ejector 220 is positioned underneath the stent 10 with the aperture 230 pointing upwards, the ejector 220 can still be in the orientation shown in FIG. 4 and gravity can be used to form a negative or positive meniscus by placing the reservoir at a height above, even, or below the exit aperture 230. Further, a low surface energy coating, such as TEFLON, can coat the aperture 230 to eliminate coating exiting the aperture except when desired. Accordingly, by using the transducer 410 during the application of the coating substance, the rate of coating dispensed can be adjusted so that certain sections of the stent 10 receive more coating than others. If the coating material is applied in an intermittent fashion, coating adjustments can be made during the stoppage of coating application. Further, the coating can be stopped while the ejector 220 is being repositioned relative to the stent 10.

The ejector 220 is aligned with a stent strut 12 and coats each individual stent strut 12. As will be discussed further below, coating flows into the ejector 220 and is ejected from the aperture 230 by the transducer 410 onto the stent strut 12, thereby limiting the coating to just the outer surface stent strut 12 and not other surfaces (e.g., the luminal surface) as in spaying and immersion techniques. In one embodiment, the sidewalls of the stent struts 12 between the outer and inner surfaces can be partially coated. Partial coating of sidewalls can be incidental, such that some coating can flow from the outer surface onto the sidewalls, or intentional.

Coupled to the ejector 220 can be a first imaging device 250 that images the stent 10 before and/or after the coating substance has been applied to a portion of the stent 10. The first imaging device 250, along with a second imaging device 260 located a distance from the stent 10, are both communicatively coupled to an optical feedback system 270 via wired or wireless techniques. The reservoir 210 may also be communicatively coupled to the optical feedback system 270 via wired or wireless techniques. Based on the imagery provided by the imaging devices 250 and 260, the optical feedback system 270 controls movement of stent 10 via the motors 30A and 30B to keep the aperture 230 aligned with the stent struts 12 and recoat the stent struts 12 if improperly (or inadequately) coated.

In an embodiment of the invention, the optical feedback system 270 includes a network of components, at least one of which performs movement while at least one other component determines the movement to be made. In an embodiment of the invention, the optical feedback system 270 can use other techniques besides optics to image a stent, such as radar or electron scanning During operation of the stent coating apparatus 200, the optical feedback system 270 causes the imaging device 260 to image the full surface of the stent 10 as the feedback system 270 causes the motor 30A to rotate the stent 10. After the initial imaging, the optical feedback system 270, using the imaging device 260, aligns the aperture 230 with a stent strut 12 by causing the motors 30A and 30B to rotate and translate the stent 10 until alignment is achieved. The optical feedback system 270 then causes the transducer 410 (FIG. 4) to dispense the coating substance through the aperture 230 by emitting acoustic energy towards coating substance located in the aperture 230. As the coating substance is dispensed, the optical feedback system 270 causes the motors 30A and 30B to rotate and translate the stent 10 in relation to the aperture 230 so as to position uncoated sections of the stent strut 12 along the aperture 230, thereby causing the entire abluminal surface of the strut 12 to be coated.

After a portion of the stent strut 12 has been coated, the optical feedback system 270 causes the transducer 410 to cease dispensing the coating substance and causes the imaging device 250 to image the stent strut 12 to determine if the strut 12 has been adequately coated. This determination can be made by measuring the difference in color and/or reflectivity of the stent strut 12 before and after the coating process. If the strut 12 has been adequately coated, then the optical feedback system 270 causes the motors 30A and 30B to rotate and translate the stent 10 so that the aperture 230 is aligned with an uncoated stent 10 section and the above process is then repeated. If the stent strut 12 is not coated adequately, then the optical feedback system 270 causes the motors 30A and 30B to rotate and translate the stent 10 and the transducer 410 to dispense the coating substance to recoat the stent strut 12. In another embodiment of the invention, the optical feedback system 270 can cause checking and recoating of the stent 10 after the entire stent 10 goes through a first coating pass.

In an embodiment of the invention, the imaging devices 250 and 260 include charge coupled devices (CCDs) or complementary metal oxide semiconductor (CMOS) devices. In an embodiment of the invention, the imaging devices 250 and 260 are combined into a single imaging device. Further, it will be appreciated by one of ordinary skill in the art that placement of the imaging devices 250 and 260 can vary as long as they have an acceptable view of the stent 10. In addition, one of ordinary skill in the art will realize that the stent mandrel fixture 20 can take any form or shape as long as it is capable of securely holding the stent 10 in place.

Accordingly, embodiments of the invention enable the fine coating of specific surfaces of the stent 10, thereby avoiding coating defects that can occur with spray coating and immersion coating methods and limiting the coating to only the abluminal surface and/or sidewalls of the stent 10. In another embodiment, the coating can be limited to depots or patterns as described in U.S. Pat. No. 6,395,326, which is incorporated herein by reference. Application of the coating in the gaps 16 between the stent struts 12 can be partially, or preferable completely, avoided.

After the brush coating of the stent 10 abluminal surface, the stent 10 can then have the inner surface coated via electrospraying or spray coating. Without masking the outer surface of the stent 10, both electrospraying and spray coating may yield some composition onto the outer surface and sidewalls of the stent 10. However, the inner surface would be substantially solely coated with a single composition different from the composition used to coat the outer surface of the stent 10. Accordingly, it will be appreciated by one of ordinary skill in the art that this embodiment enables the coating of the inner surface and the outer surface of the stent 10 with different compositions. For example, the inner surface could be coated with a composition having a bio-beneficial therapeutic substance for delivery downstream of the stent 10 (e.g., an anticoagulant, such as heparin, to reduce platelet aggregation, clotting and thrombus formation) while the outer surface of the stent 10 could be coating with a composition having a therapeutic substance for local delivery to a blood vessel wall (e.g., an anti-inflammatory drug to treat vessel wall inflammation or a drug for the treatment of restenosis).

The components of the coating substance or composition can include a solvent or a solvent system comprising multiple solvents, a polymer or a combination of polymers, a therapeutic substance or a drug or a combination of drugs. In some embodiments, the coating substance can be exclusively a polymer or a combination of polymers (e.g., for application of a primer layer or topcoat layer). In some embodiments, the coating substance can be a drug that is polymer free. Polymers can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

Representative examples of polymers that may be used include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(D-lactic acid), poly(D-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Representative examples of polymers that may be especially well suited for use include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof.

The therapeutic substance or drug can include any substance capable of exerting a therapeutic or prophylactic effect. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-l-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy) propyl-rapamycin, 40-O-[2-(2-hydroxy)ethoxy]ethyl-rapamycin, and 40-O-tetrazole-rapamycin.

Figure 3:
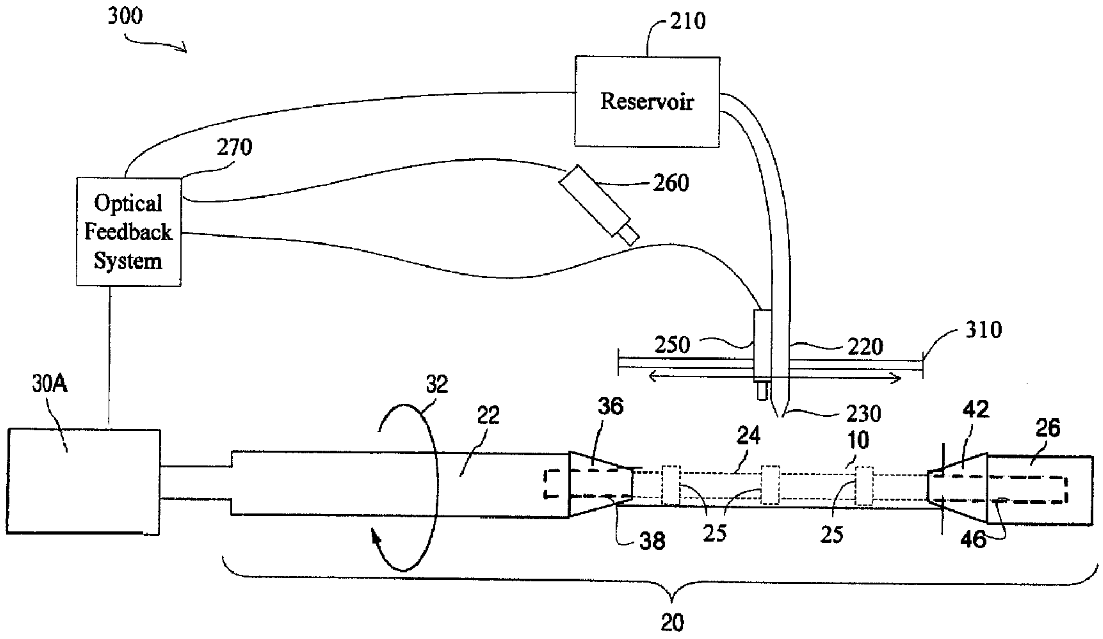
FIG. 3 is a block diagram illustrating a stent coating apparatus according to another embodiment of the invention.

FIG. 3 is a block diagram illustrating a stent coating apparatus 300 according to another embodiment of the invention. The stent coating apparatus 300 is similar to the stent coating apparatus 200. However, the ejector 220 is capable of translational movement along a guide rail 310. Accordingly, the alignment of the aperture 230 with a stent strut 12 is accomplished by the optical feedback system 270 causing the engine 30A to rotate the stent 10 in combination with causing the brush assembly 230 to move along the guard rail 310. The guard rail 310 should be at least about as long as the stent 10 to enable the ejector 220 full mobility over the length of the stent 10. In some embodiments, the ejector 220 is capable of translational movement along the guide rail 310 in combination contemporaneously or in turn with rotation and translation of the stent 10.

In another embodiment of the invention, the ejector 220 is coupled to a painting robot, such as one have six axes (three for the base motions and three for applicator orientation) that incorporates machine vision and is electrically driven. Accordingly, the ejector 220 can fully rotate around and translate along a stent 10 in a stationary position. Alternatively, both the ejector 220 and the stent 10 can rotate and/or translate contemporaneously or in turn. For example, the ejector 220 can move for alignment with a strut of the stent 10 while the stent 10 can move during coating after alignment, vice versa, or a combination of both.

In any of the above-mentioned embodiments, the coating process can be continuous, i.e., the ejector 220 can move along and coat the entire stent 10 without stopping, or move intermittently, i.e., coating a first section of the stent 10, stopping, and then aligning with a second section of the stent 10, and coating that second section. The second section may be adjacent to the first section or located a distance from the first section.

Figure 4A:
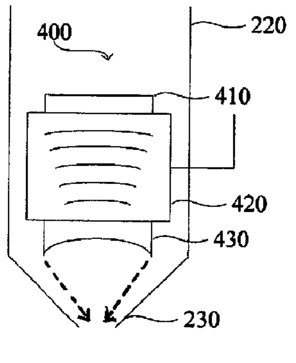
FIG. 4A and FIG. 4B (collectively, FIG. 4) are diagrams illustrating cross sections of an ejector according to an embodiment of the invention.

FIG. 4A is a diagram illustrating cross section of the ejector 220 having the aperture 230 and the transducer 410 according to an embodiment of the invention. The ejector 220 includes a transducer system 400 including the transducer 410, which can be piezoelectric, a cavity 420, and an acoustic lens 430. The transducer 410 is positioned a distance from the aperture 230. The transducer 410 converts electrical energy into unidirectional acoustic energy, which travels through the cavity 420 and is focused on the aperture 230 where the fluid meniscus is located by the acoustic lens 430. The acoustic lens 430 can be concave in shape. The focused energy causes an increase in pressure to cause droplets to drop off. The transducer 410 can include (or be coupled to) drive electronics, such as power supplies, RF amplifier, RF switches, and pulsers; an acoustic lens assembly; a fluid reservoir and level control hardware; and/or an imaging system for online monitoring for drop size and velocity. As the reservoir constantly feeds the coating substance to the ejector 220 during coating applications, the meniscus stays level, thereby preventing the need for the transducer 410 to be refocused. While the ejector 220 is shown with the aperture 230 facing downwards, it will be appreciated by one of ordinary skill in the art that the ejector 220 can employed with the aperture 230 facing upwards or otherwise positioned with respect to the stent 10.

The acoustic energy causes the ejection of drops of the coating substance due to an acoustic pressure transient at the meniscus and prevents clogging of the aperture 230 since the ejected drops do not come in contact with the aperture 230 during ejection. The acoustic energy can have a frequency of about 500 Hz to about 5000 Hz. The firing rate can range from about 1 to 3000 Hz. In an embodiment of the invention, the aperture 230 has a diameter of less than about 20 microns, leading to drops with a maximum diameter about 20 microns. In another embodiment of the invention, the aperture 230 has a diameter of about 10 microns to about 50 microns, yielding similar-sized drops. Drop volume can range from about 5 picoliters to about 30 picoliters. Drop diameter decreases exponentially as frequency increases. Pulse widths can vary from about 10 μsec to about 60 μsec.

Figure 4B:
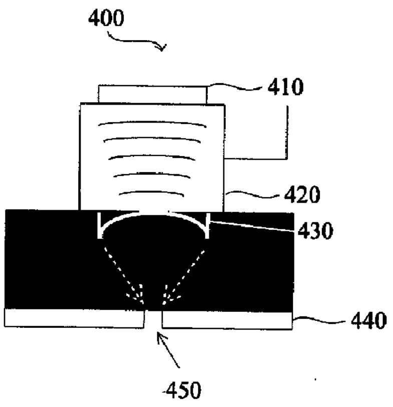

FIG. 4B is a diagram illustrating another embodiment of the transducer system 400. The transducer system 400 transmits acoustic energy to the meniscus of a coating substance (shown in black) at an aperture 450 of a plate 440.

Figure 5:
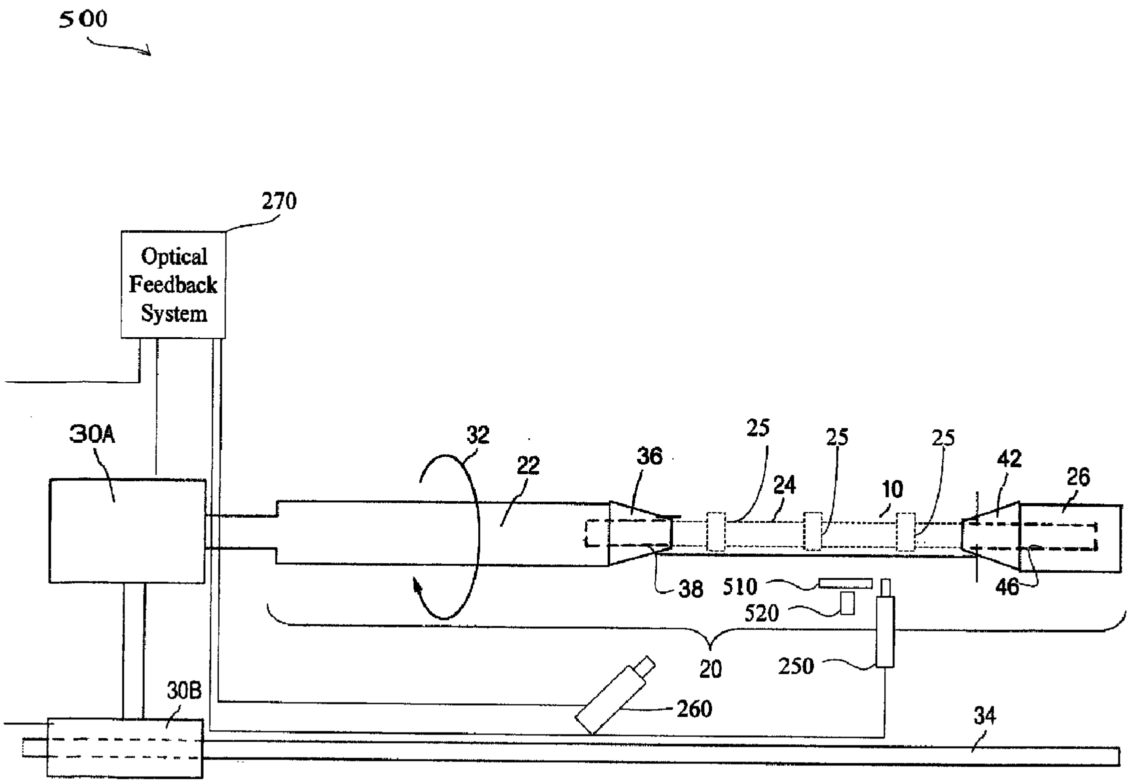
FIG. 5 is a block diagram illustrating a stent coating apparatus according to another embodiment of the invention.

FIG. 5 is a block diagram illustrating a stent coating apparatus 500 according to another embodiment of the invention. The stent coating apparatus 500 is similar to the stent coating apparatus 200. However, in place of the reservoir 210 is a reservoir housing 510 having a plurality of reservoirs 605 (FIG. 6) (e.g., wells) located beneath the stent 10. The reservoirs 605 each hold a coating substance. A transducer 520 is located beneath the reservoir housing 510 and is not in contact with the coating substance. The transducer 520 is substantially similar to the transducer 410 and transmits acoustic energy at one of the plurality of reservoirs 605 focused on the surface of the coating substance, as will be discussed in further detail below.

Figure 6:
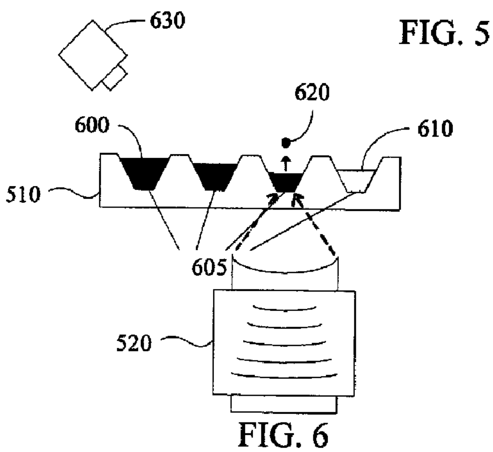
FIG. 6 is a is a diagram illustrating a cross section of an ejector according to another embodiment of the invention.

FIG. 6 is a diagram illustrating a cross section an ejector comprising the reservoir housing 510 and the transducer 520. The transducer 520 outputs acoustic energy at a reservoir 605 focused at the surface of the coating substance 600 therein. Each pulse ejects a known amount of the substance 600 in a droplet 620 from the reservoir onto the stent 10, thereby decreasing the substance 600 level in the reservoir 605. Accordingly, after each pulse of acoustic energy, the transducer 520 can be refocused to the new level in the reservoir 605. In an alternative embodiment, the reservoirs can be constantly refilled, thereby keeping the substance 600 level the same throughout the stent 10 coating process. In an embodiment of the invention, the reservoirs 605 can each hold different coating substances, e.g., a first reservoir can hold substance 600 while a second reservoir can hold substance 610. The transducer 520 can then cause the ejection of different coating substances onto the stent 10 during a single application process. Further, as there is no contact between the transducer 520 and reservoirs 605, there is no chance of cross contamination between reservoirs 605 or clogging of any ejectors.

In an embodiment of the invention, the apparatus 500 further includes a third imaging device 630 positioned to image the fluid meniscus in the reservoirs 605. The imaging device 630 is communicatively coupled to the optical feedback system 270, which is further capable of determining the height of the fluid meniscus in the reservoirs 605 and adjusting the transducer 520 accordingly (e.g., moving the transducer 520 vertically) to maintain focus on the fluid meniscus as the fluid meniscus moves to ensure optimal drop size and velocity.

Figure 7:
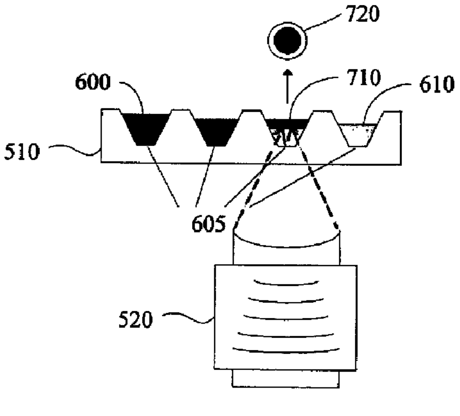
FIG. 7 is a is a diagram illustrating a cross section of an ejector according to another embodiment of the invention.

In the embodiment shown in FIG. 7, one or more of the reservoirs 605 may contain two different coating substances, e.g., the coating substance 610 and a coating substance 710. The transducer 520 ejects a combined drop 720 from the reservoir by focusing a pulse of acoustic energy at the interface between the two substances. Accordingly, the stent 10 can be coated simultaneously with two different coating substances.

Figure 8:
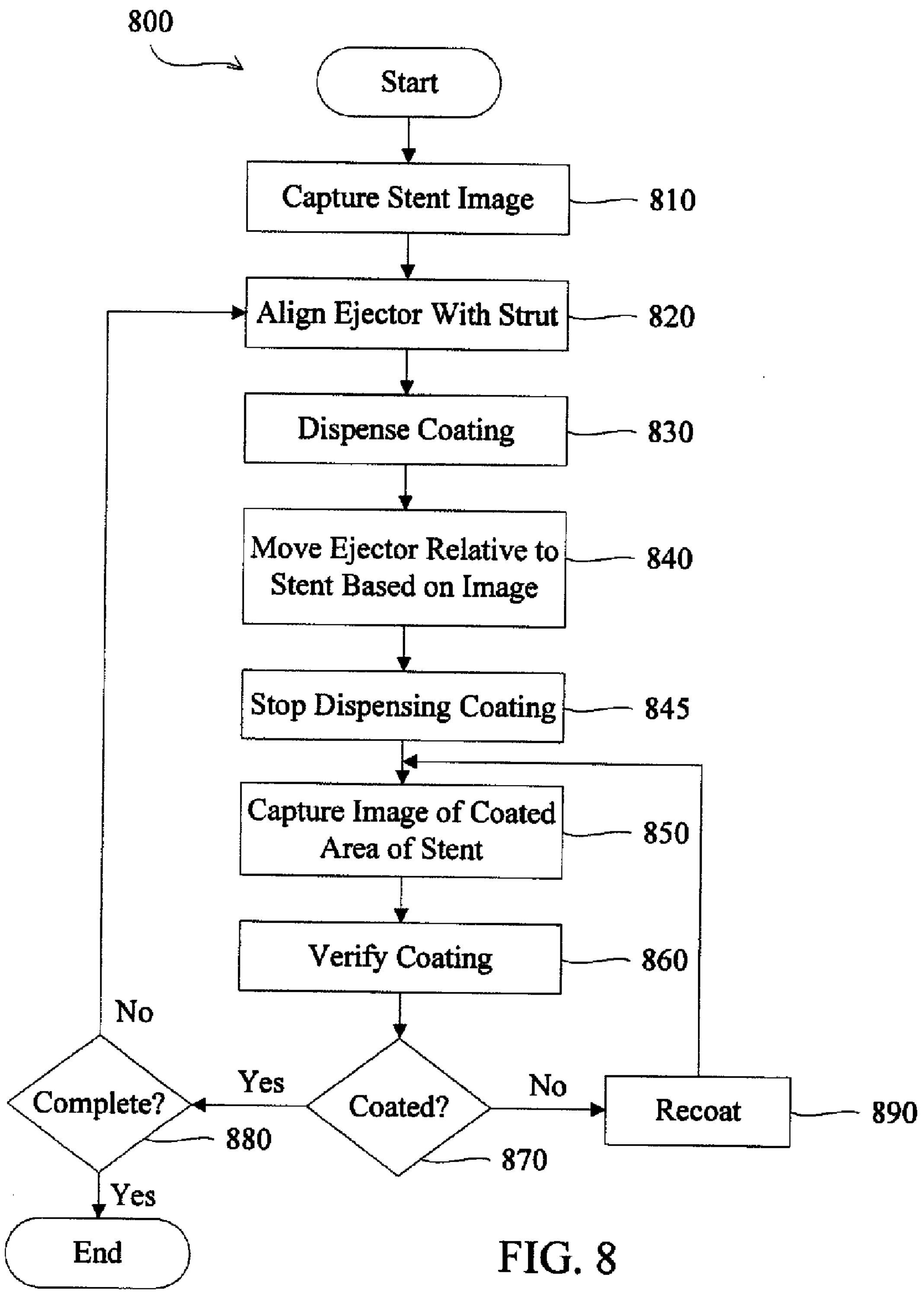
FIG. 8 is a flowchart illustrating a method of coating an abluminal stent surface.

FIG. 8 is a flowchart illustrating a method 800 of coating an abluminal stent surface. In an embodiment of the invention, the system 200, 300 or 500 can implement the method 800. First, an image of the stent 10 is captured (810) as the stent 10 is rotated. Based on the captured image, an ejector is aligned (820) with a stent strut 12 of the stent 10 via rotation and/or translation of the stent 10 and/or translation/rotation of the transducer. A coating is then dispensed (830) onto the stent via acoustic ejection of a coating substance. As the coating is being dispensed (830), the ejector and/or stent are moved (840) relative to each other so as to coat at least a portion of the stent strut 12. The coating process could involve vision guided motion such that the stent is coated as the vision system guides the stent under the nozzle or the nozzle over the stent. Alternatively, the vision system could image the entire stent first then cause the stent to move under the nozzle or the nozzle over the stent for the duration of the coating process.

The dispensing is then stopped (845), and an image of at least a portion of the stent that was just coated in captured (850). Using the captured image, the coating is verified (860) based on color change, reflectivity change, and/or other parameters. If (870) the coating is not verified (e.g., the stent strut 12 was not fully coated), then the strut 12 is recoated (890) by realigning the transducer with the strut 12, dispensing the coating, and moving the ejector relative to the strut. Capturing (850) an image and verifying (860) are then repeated.

If (870) the coating is verified and if (880) the stent has been completely coated, then the method 800 ends. Otherwise, the method 800 is repeated with a different stent strut starting with the aligned (820).

In an embodiment of the invention, the luminal surface of the stent 10 can then be coated with a different coating using electroplating or other technique. Accordingly, the abluminal surface and the luminal surface can be coated with different coatings. Further, the entire stent 10 can be coated (830) before verification (860) of the entire stent 10 or portions thereof.

While particular embodiments of the present invention have been shown and described, it will be obvious to those skilled in the art that changes and modifications can be made without departing from this invention in its broader aspects. For example, multiple reservoirs and transducers can be used simultaneously to speed up the coating of a stent. Further, the multiple reservoirs can contain different coating substances such that different coating substances can be applied to different regions of a stent substantially simultaneously. Therefore, the appended claims are to encompass within their scope all such changes and modifications as fall within the true spirit and scope of this invention.

What is claimed is:

1. A method of coating a stent, comprising:

ejecting droplets of a coating substance with a transducer from a reservoir onto a stent strut, wherein the transducer is external to a reservoir housing having a plurality of reservoir compartments and wherein energy from the transducer is focused on a fluid meniscus of the coating substance; and taking an image of the fluid meniscus to determine the height of the fluid meniscus.

2. The method of claim 1, further comprising aligning the transducer with the stent strut based on data from an optical feedback system.

3. The method of claim 2, wherein the optical feedback system causes the movement of the transducer relative to the stent strut while the coating is being ejected.

4. The method of claim 2, wherein the optical feedback system aligns the transducer with the stent strut via rotation and translation of the stent.

5. The method of claim 2, wherein the optical feedback system aligns the transducer with the stent strut via rotation of the stent and translation of the transducer.

6. The method of claim 1, further comprising determining whether the coating on the stent strut is inadequate and recoating of the stent strut when the coating is determined to be inadequate.

7. The method of claim 1, further comprising causing the transducer to move so as to maintain focus on the fluid meniscus as the fluid meniscus changes.

8. The method of claim 7, further comprising determining the height of the fluid meniscus, wherein the movement of the transducer depends on the determined height of the fluid meniscus.

9. The method of claim 1, wherein energy from the transducer is focused at the interface of the coating substance and a second coating substance in the reservoir.

10. The method of claim 1, wherein the transducer is located within an ejector holding the reservoir.

11. The method of claim 1, wherein the transducer is external to a reservoir housing holding the reservoir.

12. A method of coating a stent, comprising:

ejecting droplets of a coating substance with a transducer from a reservoir onto a stent strut, wherein energy from the transducer is focused on a fluid meniscus of the coating substance;

imaging the fluid meniscus to determine a change in the fluid meniscus; and causing the transducer to move with the fluid meniscus to maintain focus on the fluid meniscus as the fluid meniscus changes.

13. The method of claim 12, further comprising determining the height of the fluid meniscus, wherein the movement of the transducer depends on the determined height of the fluid meniscus.

14. The method of claim 12, further comprising aligning the transducer with the stent strut based on data from an optical feedback system.

* * * * *